US008569530B2

(12) United States Patent
Hippler et al.

(10) Patent No.: US 8,569,530 B2
(45) Date of Patent: Oct. 29, 2013

(54) CONVERSION OF SAPONIFIABLE LIPIDS INTO FATTY ESTERS

(75) Inventors: Jeffrey G. Hippler, Alameda, CA (US); Andy Thompson, Oakland, CA (US); Lea Dulatas, Albany, CA (US); Louis A. Kapicak, Cross Lanes, WV (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 13/078,889

(22) Filed: Apr. 1, 2011

(65) Prior Publication Data

US 2011/0313181 A1 Dec. 22, 2011

(51) Int. Cl.
*C07C 51/09* (2006.01)
*C11C 3/00* (2006.01)
*C12P 7/64* (2006.01)

(52) U.S. Cl.
USPC .......................................... 554/170; 435/134

(58) Field of Classification Search
USPC .......................................... 554/170; 435/134
See application file for complete search history.

(56) References Cited

U.S. PATENT DOCUMENTS 1,926,780 A 9/1933 Lippincott
2,730,190 A 1/1956 Brown et al.
2,766,203 A 10/1956 Brown et al.
3,468,057 A 9/1969 Buisson et al.
3,897,000 A 7/1975 Mandt
3,962,466 A 6/1976 Nakabayashi
4,003,337 A 1/1977 Moore
4,159,944 A 7/1979 Erickson et al.
4,253,271 A 3/1981 Raymond
4,267,038 A 5/1981 Thompson
4,341,038 A 7/1982 Bloch et al.
4,365,938 A 12/1982 Warinner
4,535,060 A 8/1985 Comai
4,658,757 A 4/1987 Cook
5,105,085 A 4/1992 McGuire et al.
5,130,242 A 7/1992 Barclay
5,180,499 A 1/1993 Hinson et al.
5,244,921 A 9/1993 Kyle et al.
5,275,732 A 1/1994 Wang et al.
5,338,673 A 8/1994 Thepenier et al.

(Continued)

FOREIGN PATENT DOCUMENTS

JP 2004300218 10/2001
JP 2008280252 11/2008

(Continued)

OTHER PUBLICATIONS

Chem. Abstr.—Loury, Maurice, Method for rapid conversion of fats to methyl esters, Revue Francaise des Corps Gras (1967), 14(6), 383-9.*

(Continued)

*Primary Examiner* — Deborah D Carr
(74) *Attorney, Agent, or Firm* — Carr & Ferrell LLP

(57) ABSTRACT

Various embodiments of the present invention are directed to processes and methods for converting lipids comprising fatty acids into fatty esters. According to various embodiments of the invention, the saponifiable lipids are reacted with a base to form alkali soaps. The alkali soaps are then reacted with an acid to form fatty esters. Both the base reaction and the acid reaction may occur in the presence of one or more alcohols. Following the acid reaction, a solvent may be added to effect a separation of the fatty esters, which may then be recovered.

19 Claims, 2 Drawing Sheets

(56) References Cited

U.S. PATENT DOCUMENTS

| | | | |
|---|---|---|---|
| 5,478,208 | A | 12/1995 | Kasai et al. |
| 5,527,456 | A | 6/1996 | Jensen |
| 5,539,133 | A | 7/1996 | Kohn et al. |
| 5,567,732 | A | 10/1996 | Kyle et al. |
| 5,658,767 | A | 8/1997 | Kyle |
| 5,661,017 | A | 8/1997 | Dunahay et al. |
| 5,668,298 | A | 9/1997 | Waldron |
| 5,776,349 | A | 7/1998 | Guelcher et al. |
| 6,117,313 | A | 9/2000 | Goldman et al. |
| 6,143,562 | A | 11/2000 | Trulson et al. |
| 6,166,231 | A | 12/2000 | Hoeksema |
| 6,372,460 | B1 | 4/2002 | Gladue et al. |
| 6,524,486 | B2 | 2/2003 | Borodyanski et al. |
| 6,579,714 | B1 | 6/2003 | Hirabayashi et al. |
| 6,736,572 | B2 | 5/2004 | Geraghty |
| 6,750,048 | B2 | 6/2004 | Ruecker et al. |
| 6,768,015 | B1 | 7/2004 | Luxem et al. |
| 6,831,040 | B1 | 12/2004 | Unkefer et al. |
| 7,381,326 | B2 | 6/2008 | Haddas |
| 7,582,784 | B2 | 9/2009 | Banavali et al. |
| 7,767,837 | B2 | 8/2010 | Elliott |
| 7,868,195 | B2 | 1/2011 | Fleischer et al. |
| 7,883,882 | B2 | 2/2011 | Franklin et al. |
| 8,404,473 | B2 | 3/2013 | Kilian et al. |
| 2003/0199490 | A1 | 10/2003 | Antoni-Zimmermann et al. |
| 2004/0121447 | A1 | 6/2004 | Fournier |
| 2004/0161364 | A1 | 8/2004 | Carlson |
| 2004/0262219 | A1 | 12/2004 | Jensen |
| 2005/0048474 | A1 | 3/2005 | Amburgey |
| 2005/0064577 | A1 | 3/2005 | Berzin |
| 2005/0164192 | A1 | 7/2005 | Graham et al. |
| 2005/0170479 | A1 | 8/2005 | Weaver et al. |
| 2005/0260553 | A1 | 11/2005 | Berzin |
| 2005/0273885 | A1 | 12/2005 | Singh et al. |
| 2006/0045750 | A1 | 3/2006 | Stiles et al. |
| 2006/0101535 | A1 | 5/2006 | Forster et al. |
| 2006/0122410 | A1 | 6/2006 | Fichtali et al. |
| 2006/0166243 | A1 | 7/2006 | Su et al. |
| 2007/0102371 | A1 | 5/2007 | Bhalchandra et al. |
| 2008/0118964 | A1 | 5/2008 | Huntley et al. |
| 2008/0120749 | A1 | 5/2008 | Melis et al. |
| 2008/0155888 | A1 | 7/2008 | Vick et al. |
| 2008/0160591 | A1 | 7/2008 | Wilson et al. |
| 2008/0160593 | A1 | 7/2008 | Oyler |
| 2008/0194029 | A1 | 8/2008 | Hegemann et al. |
| 2008/0268302 | A1 | 10/2008 | McCall |
| 2008/0275260 | A1 | 11/2008 | Elliott |
| 2008/0293132 | A1 | 11/2008 | Goldman et al. |
| 2009/0011492 | A1 | 1/2009 | Berzin |
| 2009/0029445 | A1 | 1/2009 | Eckelberry et al. |
| 2009/0081748 | A1 | 3/2009 | Oyler |
| 2009/0148931 | A1 | 6/2009 | Wilkerson et al. |
| 2009/0151241 | A1 | 6/2009 | Dressler et al. |
| 2009/0162919 | A1 | 6/2009 | Radaelli et al. |
| 2009/0234146 | A1 | 9/2009 | Cooney et al. |
| 2009/0317857 | A1 | 12/2009 | Vick et al. |
| 2009/0317878 | A1 | 12/2009 | Champagne et al. |
| 2009/0317904 | A1 | 12/2009 | Vick et al. |
| 2009/0325270 | A1 | 12/2009 | Vick et al. |
| 2010/0022393 | A1 | 1/2010 | Vick |
| 2010/0068772 | A1 | 3/2010 | Downey |
| 2010/0151540 | A1 | 6/2010 | Gordon et al. |
| 2010/0183744 | A1 | 7/2010 | Weissman et al. |
| 2010/0196995 | A1 | 8/2010 | Weissman et al. |
| 2010/0210003 | A1 | 8/2010 | King et al. |
| 2010/0210832 | A1 | 8/2010 | Kilian et al. |
| 2010/0260618 | A1 | 10/2010 | Parsheh et al. |
| 2010/0261922 | A1 | 10/2010 | Fleischer et al. |
| 2010/0314324 | A1 | 12/2010 | Rice et al. |
| 2010/0317088 | A1 | 12/2010 | Radaelli et al. |
| 2010/0327077 | A1 | 12/2010 | Parsheh et al. |
| 2010/0330643 | A1 | 12/2010 | Kilian et al. |
| 2010/0330658 | A1 | 12/2010 | Fleischer et al. |
| 2011/0041386 | A1 | 2/2011 | Fleischer et al. |
| 2011/0070639 | A1 | 3/2011 | Pandit et al. |
| 2011/0072713 | A1 | 3/2011 | Fleischer et al. |
| 2011/0136212 | A1 | 6/2011 | Parsheh et al. |
| 2011/0196163 | A1 | 8/2011 | Fleischer et al. |
| 2011/0197306 | A1 | 8/2011 | Bailey et al. |
| 2011/0300568 | A1 | 12/2011 | Parsheh et al. |
| 2011/0313181 | A1 | 12/2011 | Thompson et al. |

FOREIGN PATENT DOCUMENTS

| | | |
|---|---|---|
| WO | WO2004106238 | 12/2001 |
| WO | WO 2009/037683 | 3/2009 |
| WO | W02011/053867 A1 | 5/2011 |

OTHER PUBLICATIONS

Cravotto et al., Improved extraction of vegetable oils under high-intensity ultrasound and/or microwaves, Ultrasonics Sonochemistry 15:898-9002 (2008).

Endo et al. "Inactivation of Blasticidin S by *Bacillus cereus* II. Isolation and Characterization of a Plasmid, pBSR 8, from *Bacillus cereus*," The Journal of Antibiotics 41 (2): 271-2589-2601.

Felix, R. "Use of the cell wall-less alga *Dunaliella bioculata* in herbicide screening tests" Annals of Applied Biology, 113, 1988, pp. 55-60.

Grima et al. "Recovery of Microalgal Biomass in Metabolites: Process Options and Economics "Biotechnology Advances 20 (2003) 491-515.

Hallmann et al., "Genetic Engineering of the Multicellular Green Alga *Volvox*: a Modified and Multiplied Bacterial Antibiotic Resistance Gene as a Dominant Selectable Marker"The Plant Journal 17(1): 99-109 (Jan. 1999).

Hedenskog, G., et al., Investigation of some Methods for Increasing the Digestibility in Vitro of Microalgae, 1969, Biotechnology and Bioengineering, vol. XI, pp. 37-51.

Kindle et al. "Stable Nuclear Transformation of *Chlamydomonas* Using the *Chlamydomonas* Gene for Nitrate Reductase" The Journal of Cell Biology 109 (6, part 1): 2589-2601.

Knuckey et al. "Production of Microalgal Concentrates by Flocculation and their Assessment as Aquaculture Feeds, " Aquaculturel Engineering 35 (2006) 300-313.

NCBI entry EE109892 (Jul. 27, 2006) [Retrieved from the Internet on Oct. 19, 2009; <http://www.ncbi.nlm.nih.gov/nucest/EE109892?ordinapos=1&itoo1=EntrezSystem2.Pentrez.Sequence.Sequence_ResultsPanel. Sequence_RVDocSum.].

Prein et al. "A Novel Strategy for Constructing N-Terminal Chromosomal Fusions to Green Fluorescent Protein in the Yeast *Saccharomyces cerevisiae*" FEBS Letters 485 (2000) 29-34.

Santin-Montanaya I. "Optimal Growth of *Dunaliella primolecta* in axenic conditions to assay herbicides" Chemosphere, 66, Elsevier 2006, pp. 1315-1322.

Schiedlmeier et al., "Nuclear Transformation of *Volvox carteri*" Proceedings of the National Academy of Sciences USA 91(11): 5080-5084 (May 1994).

Wendland et al. "PCR-Based Methods Facilitate Targeted Gene Manipulations and Cloning Procedures" Curr.Gen. (2003) 44:115-123.

Non-Final Office Action, mailed Dec. 7, 2011, U.S. Appl. No. 12/495,581, filed Jun. 30, 2009.

Notice of Allowance, mailed Aug. 9, 2012, U.S. Appl. No. 12/495,581, filed Jun. 30, 2009.

Notice of Allowance, mailed Nov. 23, 2012 U.S. Appl. No. 12/495,581, filed Jun. 30, 2009.

Non-Final Office Action, mailed May 19, 2011, U.S. Appl. No. 12/485,027, filed Jun. 15, 2009.

Non-Final Office Action, mailed Sep. 18, 2012, U.S. Appl. No. 12/485,847, filed Jun. 16, 2009.

Notice of Allowance, mailed Sep. 13, 2010, U.S. Appl. No. 12/610,134, filed Oct. 30, 2009.

Non-Final Office Action, mailed Nov. 9, 2010, U.S. Appl. No. 11/985,183, filed Nov. 13, 2007.

Notice of Allowance, filed Apr. 29, 2011, U.S. Appl. No. 11/985,183, filed Nov. 13, 2007.

(56) References Cited

OTHER PUBLICATIONS

Notice of Allowance, mailed Aug. 18, 2011, U.S. Appl. No. 11/985,183, filed Nov. 13, 2007.
Non-Final Office Action, mailed Jan. 6, 2012, U.S. Appl. No. 12/339,521, filed Dec. 19, 2008.
Non-Final Office Action, mailed Feb. 28, 2011, U.S. Appl. No. 12/494,170, filed Jun. 29, 2009.
Final Office Action, mailed Sep. 23, 2011, U.S. Appl. No. 12/494,170, filed Jun. 29, 2009.
Notice of Allowance, mailed Sep. 21, 2012, U.S. Appl. No. 12/494,170, filed Jun. 29, 2009.
Notice of Allowance, mailed Jan. 18, 2013, U.S. Appl. No. 12/494,170, filed Jun. 29, 2009.
Non-Final Office Action, maield Dec. 29, 2011, U.S. Appl. No. 12/544,079, filed Aug. 19, 2009.
Final Office Action, mailed Sep. 6, 2012, U.S. Appl. No. 12/544,079, filed Aug. 19, 2009.
Advisory Action, mailed, Nov. 15, 2012, U.S. Appl. No. 12/544,079, filed Aug. 19, 2009.
Non-Final Office Action, mailed Jan. 26, 2012, U.S. Appl. No. 12/571,229, filed Sep. 30, 2009.
Final Office Action, mailed Sep. 19, 2012, U.S. Appl. No. 12/571,229, filed Sep. 30, 2009.
Advisory Action, mailed Nov. 27, 2012, U.S. Appl. No. 12/571,229 Sep. 30, 2009.
Non-Final Office Action, mailed Jan. 18, 2013, U.S. Appl. No. 12/983,767, filed Jan. 3, 2011.
Non-Final Office Action, mailed Jan. 31, 2013, U.S. Appl. No. 13/075,122, filed Mar. 29, 2011.
Non-Final Office Action, mailed Oct. 27, 2011, U.S. Appl. No. 13/078,889, filed Apr. 1, 2011.
Final Office Action, mailed Jun. 29, 2012, U.S. Appl. No. 13/078,889, filed Apr. 1, 2011.
Notice of Allowance, mailed Feb. 25, 2013, U.S. Appl. No. 13/078,889, filed Apr. 1, 2011.
Notice of Allowance, mailed Mar. 20, 2013, U.S. Appl. No. 13/078,889, filed Apr. 1, 2011.
International Search Report, mailed Jan. 6, 2011, PCT/US2010/054861, Oct. 29, 2010.
Janssen, M. "Phytosynthetic efficiency of Dunaliella tertiolecta under short light/dark cycles," Enzyme and Microbial Technology, 29, 2001, p. 298-305.
Saenz, Me., "Effects of Technical Grade and a Commercial Formulation of Glyphosate on Algal Population Growth," Bulletin of Environmental Contamination Toxicology, 1997, 59: pp. 638-644.
Molnar et al., "Highly Specific Gene Silencing by Artificial MicroRNAs in the Unicellular Agla Chlamydomonas reinhardtii," Plant Jour. ePub 17 Jan. 2009, vol. 58, No. 1, pp. 157-164 (Abstract Only).
Chen et al., "Conditional Production of a Functional Fish Growth Hormonal in the Transgenic Line of Nannochloropsis oculata (Eustigmatophyceae)," J. Phycol. Jun. 2008, vol. 44, No. 3, pp. 768-776.
Nelson et al., "Targeted Disruption of NIT8 Gene in Chlamydomonas reinhardtii." Mol. Cell. Bio. Oct. 1995, vol. 15, No. 10, pp. 5762-5769.
Kureshy et al., "Effect of Ozone Treatment on Cultures of Nannochloropsis oculata, Isochrysis galbana, and Chaetoceros gracilis," Journal of the World Aquaculture Society, 1999, 30(4), pp. 473-480.
Csogor et al., "Light Distribution in a Novel Photobioreactor -Modelling for Optimization," Journal of Applied Phycology, vol. 13, pp. 325-333.
Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.
Zittelli et al., "Mass Cultivation of Nannochloropsis Sp. In Annular Reactors," Journal of Applied Phycology, vol. 15, pp. 107-113, Mar. 2003.
Strzepek et al., "Photosynthetic Architecture Differs in Coastal and Oceanic Diatoms," Nature, vol. 431, pp. 689-692, Oct. 2004.
Lee et al., "Isolation and Characterization of a Xanthophyll Aberrant Mutant of the Green Alga Nannochloropsis oculata," Marine Biotechnology, 2006, vol. 8, pp. 238-245.
Berberoglu et al., "Radiation Characteristics of Chlamydomonas reinhardtii CC125 and its truncated chlorophyll antenna transformants tla1, tlaX, and tial-CW+,"0 International Journal of Hydrogen Energy, 2008, vol. 33, pp. 6467-6483.
Ghirardi et al., "Photochemical Apparatus Organization in the Thylakoid Membrane of Hordeum vulgare wild type and chlorophyll b-less chlorina f2 mutant," Biochimica et Biophysica Act (BBA)—Bioengergetics, vol. 851, Issue 3, Oct. 1986, pp. 331-339 (abstract only).
Steinitz et al., "A mutant of the cyanobacterium Plectonema boryanum resistant to photooxidation," Plant Science Letters, vol. 16, Issues 2-3, 1979, pp. 327-335 (abstract only).
Koller et al., "Light Intensity During Leaf Growth Affects Chlorophyll Concentration and CO2 Assimilation of a Soybean Chlorophyll Mutant," Crop Science, 1974, vol. 14, pp. 779-782 (abstract only).
Shikanai et al., "Identification and Characterization of Arabidopsis Mutants with Reduced Quenching of Chlorophyll Fluorescence," Plant and Cell Physiology, 1999, vol. 40, No. 11, pp. 1134-1142 (abstract only).
Ben-Amotz, Ami. "Large-Scale Open Algae Ponds," presented at the NREL-AFOSR Joint Workshop on Algal Oil for Get Fuel Production in Feb. 2008.
Ebeling et al., "Design and Operation of a Zero-Exchange Mixed-Cell Raceway Production System," 2nd Int'l Sustainable Marine Fish Culture Conference and Workshop, Oct. 2005.
Ebeling et al., "Mixed-Cell Raceway: Engineering Design Criteria, Construction, and Hydraulic Characterization," North American Journal of Aquaculture, 2005, 67: 193-201 (abstract only).
Labatut et al., "Hydrodynamics of a Large-Scale Mixed-Cell Raceway (MCR): Experimental Studies," Aquacultural Engineering vol. 37, Issue 2, Sep. 2007, pp. 132-143.
Kizilisoley et al., "Micro-Algae Growth Technology Systems," Presented by Selim Helacioglu, Soley Institute, 2008.
Dunstan et al., "Changes in the Lipid Composition and Maximisation of the Polyunsaturated Fatty Acid Content of Three Microalgae Grown in Mass Culture," Journal of Applied Phycology, 5, pp. 71-83, 1993.
Carvalheiro et al., "Hemicellulose Biorefineries: A Review on Biomass Pretreatments," Journal of Scientific & Industrial Research, vol. 67, Nov. 2008, pp. 849-864.
Lotero et al., "Synthesis of Biodiesel via Acid Catalysis," Ind. Eng. Chem. Res., 2005, pp. 5353-5363.
Gouveia et al., "Microalgae as a raw material for biofuels production," J. Ind. Microbiol. Biotechnol, 2009, vol. 36, 269-274.
International Search Report and Written Opinion of the International Searching Authority mailed Jan. 6, 2011 for Application No. PCT/US2010/054861, filed Oct. 29, 2010.
Chen et al. "Subcritical co-solvents extraction of lipid from wet microalgae pastes of Nannochloropsis sp.," Eur. J. Lipid Sci. Technol., vol. 114, 2012, pp. 205-212.
Wang et al., "Lipid and Biomass Distribution and Recovery from Two Microalgae by Aqueous and Alcohol Processing," Journal of the American Oil Chemists' Society, vol. 38, Issue 2, Jul. 2011, pp. 335-345.
Pitipanapong et al., "New approach for extraction of charantin from Momordica charantia with pressurized liquid extraction," Separation and Purification Technology, vol. 52, Issue 3, Jan. 2007.

* cited by examiner

CONVERSION OF SAPONIFIABLE LIPIDS INTO FATTY ESTERS

FIELD OF THE INVENTION

The present invention is directed to systems and methods for producing fatty esters from saponifiable lipids.

SUMMARY OF THE INVENTION

Various embodiments of the present invention include systems and methods for converting a variety of lipids comprising fatty acids into esters. An exemplary method comprises first treating the lipids comprising fatty acids with a mixture of a base and a first alcohol to form alkali soaps. The alkali soaps are then reacted with a mixture of a second alcohol and an acid to form fatty esters. Following the acid reaction, a solvent may be added to separate the fatty esters from the reaction mixture.

DETAILED DESCRIPTION

Figure 1:
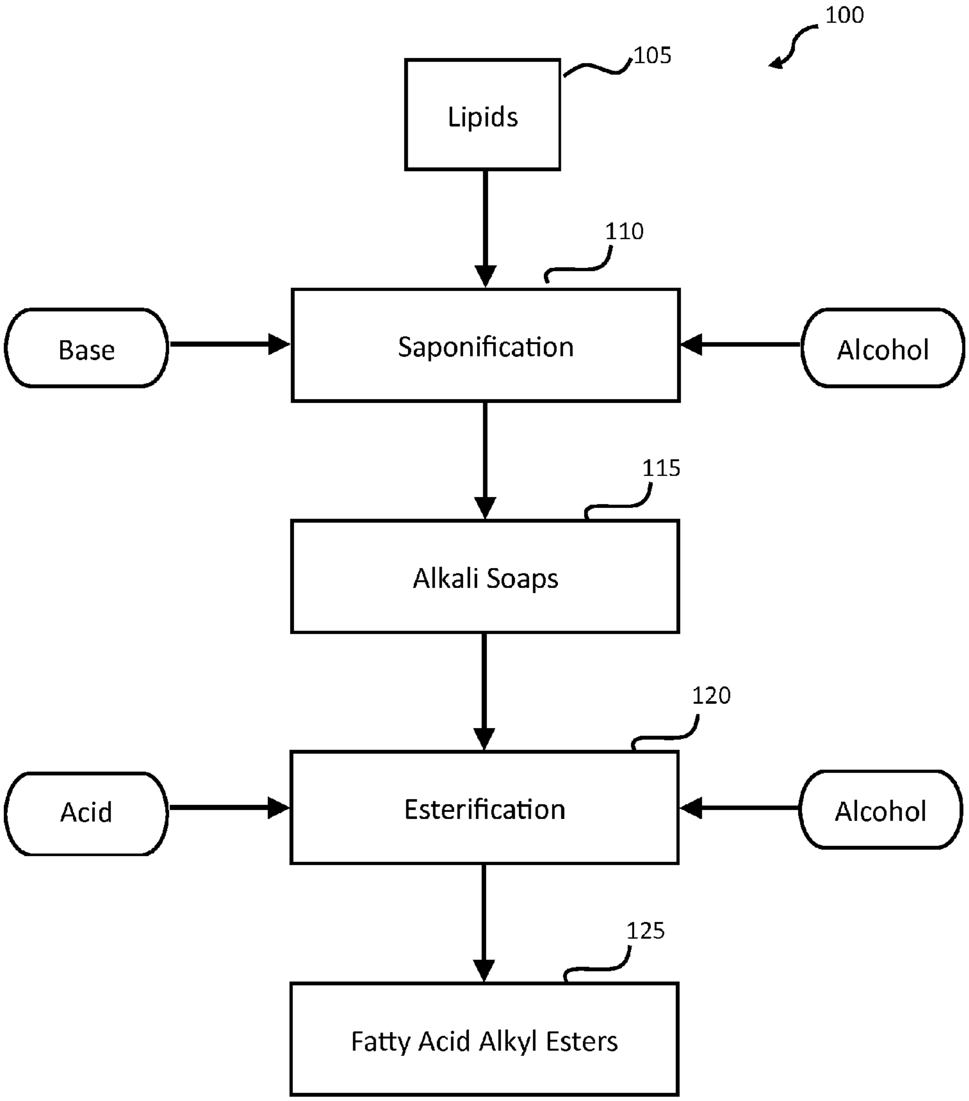
FIG. 1 is a general flow chart of an exemplary method for producing fatty esters according to various embodiments of the present invention.

Various embodiments of the present invention are directed to processes and methods for converting lipids comprising fatty acids into fatty esters. According to various embodiments of the invention, the lipids are first reacted with a base to form alkali soaps. The alkali soaps are then reacted with an acid to form fatty esters. Both the base reaction and the acid reaction occur in the presence of one or more alcohols. Following the acid reaction, a solvent may be added to separate the fatty esters, which may then be recovered.

Lipids are a broad class of chemical compounds that may be defined as "fatty acids and their derivatives, and substances related biosynthetically or functionally to these compounds" [W. W. Christie, *Gas Chromatography and Lipids: A Practical Guide* (1989), p. 5]. Most lipids are soluble in organic solvents, but many are insoluble in water; however, given the diverse nature of lipids, some compounds regarded as lipids may also be soluble in water. Organic solvents in which lipids are soluble are generally non-polar solvents and may include pentane, cyclopentane, hexane, cyclohexane, benzene, toluene, 1,4-dioxane, chloroform, diethyl ether, methylene chloride, ethyl acetate, d-limonene, heptane, naphtha, and xylene, among others. Higher melting point lipids are typically solids at room temperature and are broadly classified as fats or waxes. Lipids with lower melting points are typical liquids at room temperature and are broadly classified as oils.

Comprehensive classification of lipids is difficult because of their diverse nature. One classification system for biological lipids is based on the biochemical subunits from which the lipids originate. This system provides for various general categories of biological lipids, including fatty acyls, glycerolipids, glycerophospholipids, sphingolipids, saccharolipids, sterol lipids, and glycolipids.

Fatty acyls (or fatty acids and their conjugates and derivatives) are carbon compounds that may be naturally synthesized via condensation of malonyl coenzyme A units by a fatty acid synthase complex. Fatty acyls typically have a carbon chain comprised of 4 to 24 carbon atoms, and often terminate with a carboxyl group (—COOH). Lipids containing fatty acyls can be hydrolyzed into alkali fatty acid salts using basic hydrolysis, a process known as saponification. Fatty acyls may be saturated or unsaturated, and may also include functional groups containing oxygen, nitrogen, sulfur, and halogens. Fatty acyls found in plant tissues commonly have a carbon chain comprised of 14, 16, 18, 20, 22, or 24 carbon atoms.

Common fatty acyls of plant and animal origin can be divided into three broad categories of saturated fatty acids, monoenoic fatty acids, and polyunsaturated fatty acids. Saturated fatty acids are characterized as having 2 or more carbon atoms in the carbon chain with no double bonds between any of the carbon atoms. Example saturated fatty acids include ethanoic acid, butanoic acid, hexanoic acid, octanoic acid, decanoic acid, dodecanoic acid, tetradecanoic acid, hexadecanoic acid, octadecanoic acid, eicosanoic acid, docosanoic acid, and tetracosanoic acid. Monoenoic fatty acids are characterized as having a single carbon-carbon double bond in the carbon chain. The double bond is typically a cis-configuration, although some trans-configuration compounds are known. Example monoenoic fatty acids include cis-9-hexadecenoic acid, cis-6-octadecenoic acid, cis-9-octadecenoic acid, cis-11-octadecenoic acid, cis-13-docosenoic acid, and cis-15-tetracosenoic acid. Polyunsaturated fatty acids are characterized as having two or more carbon double bonds in the carbon chain. Example polyunsaturated fatty acids include 9,12-octadecadienoic acid, 6,9,12-octadecatrienoic acid, 9,12,15-octadecatrienoic acid, 5,8,11,14-eicosatetraenoic acid, 5,8,11,14,17-eicosapentaenoic acid, and 4,7,10,13,16,19-docosahexanoic acid.

Glycerolipids may be formed by joining fatty acids to glycerol by ester bonds. The majority of glycerolipids are formed by mono-, di-, or tri-substitution of fatty acids on the glycerol molecule. The most common naturally occurring glycerolipids are of the tri-substituted variety, known as triacylglycerols or triglycerides. Example glycerolipids include monoradylglycerols, monoacylglycerols, monoalkylglycerols, mono-(1Z-alkenyl)-glycerols, diradylglycerols, diacylglycerols, 1-alkyl,2-acylglycerols, 1-acyl,2-alkylglycerols, dialkylglycerols, 1Z-alkenylacylglycerols, di-glycerol tetraethers, di-glycerol tetraether glycans, triradylglycerols, triacylglycerols, alkyldiacylglycerols, dialkylmonoacylglycerols, 1Z-alkenyldiacylglycerols, estolides, glycosylmonoradylglycerols, glycosylmonoacylglycerols, glycosylmonoalkylglycerols, glycosyldiradylglycerols, glycosyldiacylglycerols, glycosylalkylacylglycerols, and glycosyldialkylglycerols.

Glycerophospholipids (or simply phospholipids) may be characterized by fatty acids linked through an ester oxygen to the first and second carbons atoms of the glycerol molecule, with a phosphate functional group ester-linked to the third carbon atom of the glycerol molecule. Other functional groups may also be linked to the phosphate functional group. In plant and animal cells, glycerophospholipids may serve as structural components of the cell membrane. Example glycerophospholipids include phosphatidylcholine (lecithin), phosphatidylethanolamine (cephalin), phosphatidylinositol, phosphatidylserine, bisphosphatidylglycerol (cardiolipin), glycerophosphocholines, diacylglycerophosphocholines, 1-alkyl,2-acylglycerophosphocholines, 1-acyl,2-alkylglycerophosphocholines, 1Z-alkenyl,2-acylglycerophosphocholines, dialkylglycerophosphocholines, monoacylglycerophosphocholines, monoalkylglycerophosphocholines, 1Z-alkenylglycerophosphocholines, glycerophosphoethanolamines, diacylglycerophosphoethanolamines, 1-alkyl,2-acylglycerophosphoethanolamines, 1-acyl,2-alkylglycerophosphoethanolamines, 1Z-alkenyl,2-acylglycerophosphoethanolamines, dialkylglycerophosphoethanolamines, monoacylglycerophosphoethanolamines, monoalkylglycerophosphoethanolamines, 1Z-alkenylglycerophosphoethanolamines, glycerophosphoserines, diacylglycerophosphoserines, 1-alkyl,2-acylglycerophosphoserines, 1Z-alkenyl,2-acylglycerophosphoserines, dialkylglycerophosphoserines, monoacylglycerophosphoserines, monoalkylglycerophosphoserines, 1Z-alkenylglycerophosphoserines, glycerophosphoglycerols, diacylglycerophosphoglycerols, 1-alkyl,2-acylglycerophosphoglycerols, 1-acyl,2-alkylglycerophosphoglycerols, 1Z-alkenyl,2-acylglycerophosphoglycerols, dialkylglycerophosphoglycerols, monoacylglycerophosphoglycerols, monoalkylglycerophosphoglycerols, 1Z-alkenylglycerophosphoglycerols, diacylglycerophosphodiradylglycerols, diacylglycerophosphomonoradylglycerols, monoacylglycerophosphomonoradylglycerols, glycerophosphoglycerophosphates, diacylglycerophosphoglycerophosphates, 1-alkyl,2-acylglycerophosphoglycerophosphates, 1Z-alkenyl,2-acylglycerophosphoglycerophosphates, dialkylglycerophosphoglycerophosphates, monoacylglycerophosphoglycerophosphates, monoalkylglycerophosphoglycerophosphates, 1Z-alkenylglycerophosphoglycerophosphates, glycerophosphoinositols, diacylglycerophosphoinositols, 1-alkyl,2-acylglycerophosphoinositols, 1Z-alkenyl,2-acylglycerophosphoinositols, dialkylglycerophosphoinositols, monoacylglycerophosphoinositols, onoalkylglycerophosphoinositols, 1Z-alkenylglycerophosphoinositols, glycerophosphoinositol monophosphates, diacylglycerophosphoinositol monophosphates, 1-alkyl,2-acylglycerophosphoinositol monophosphates, 1Z-alkenyl,2-acylglycerophosphoinositol monophosphates, dialkylglycerophosphoinositol monophosphates, monoacylglycerophosphoinositol monophosphates, monoalkylglycerophosphoinositol monophosphates, 1Z-alkenylglycerophosphoinositol monophosphates, glycerophosphoinositol bisphosphates, diacylglycerophosphoinositol bisphosphates, 1-alkyl,2-acylglycerophosphoinositol bisphosphates, 1Z-alkenyl,2-acylglycerophosphoinositol bisphosphates, monoacylglycerophosphoinositol bisphosphates, onoalkylglycerophosphoinositol bisphosphates, 1Z-alkenylglycerophosphoinositol bisphosphates, glycerophosphoinositol trisphosphates, diacylglycerophosphoinositol trisphosphates, 1-alkyl,2-acylglycerophosphoinositol trisphosphates, 1Z-alkenyl,2-acylglycerophosphoinositol trisphosphates, monoacylglycerophosphoinositol trisphosphates, monoalkylglycerophosphoinositol trisphosphates, 1Z-alkenylglycerophosphoinositol trisphosphates, glycerophosphates, diacylglycerophosphates, 1-alkyl,2-acylglycerophosphates, 1Z-alkenyl,2-acylglycerophosphates, dialkylglycerophosphates, monoacylglycerophosphates, monoalkylglycerophosphates, 1Z-alkenylglycerophosphates, glyceropyrophosphates, diacylglyceropyrophosphates, monoacylglyceropyrophosphates, glycerophosphoglycerophosphoglycerols, diacylglycerophosphoglycerophosphodiaradylglycerols, diacylglycerophosphoglycerophosphomonoradylglycerols, 1-alkyl,2-acylglycerophosphoglycerophosphodiradylglycerols, 1-alkyl,2-acylglycerophosphoglycerophosphomonoradylglycerols, 1Z-alkenyl,2-acylglycerophosphoglycerophosphodiradylglycerols, 1Z-alkenyl,2-acylglycerophosphoglycerophosphomonoradylglycerols, dialkylglycerophosphoglycerophosphodiradylglycerols, dialkylglycerophosphoglycerophosphomonoradylglycerols, monoacylglycerophosphoglycerophosphomonoradylglycerols, monoalkylglycerophosphoglycerophosphomonoradylglycerols, 1Z-alkenylglycerophosphoglycerophosphodiradylglycerols, 1Z-alkenylglycerophosphoglycerophosphomonoradylglycerols, CDP-glycerols, CDP-diacylglycerols, CDP-1-alkyl,2-acylglycerols, CDP-1Z-alkenyl,2-acylglycerols, CDP-dialkylglycerols, CDP-monoacylglycerols, CDP-monoalkylglycerols, CDP-1 Z-alkenylglycerols, glycosylglycerophospholipids, diacylglycosylglycerophospholipids, 1-alkyl,2-acylglycosylglycerophospholipids, 1Z-alkenyl,2-acylglycosylglycerophospholipids, dialkylglycosylglycerophospholipids, monoacylglycosylglycerophospholipids, monoalkylglycosylglycerophospholipids, 1Z-alkenylglycosylglycerophospholipids, glycerophosphoinositolglycans, diacylglycerophosphoinositolglycans, 1-alkyl,2-acylglycerophosphoinositolglycans, 1Z-alkenyl,2-acylglycerophosphoinositolglycans, monoacylglycerophosphoinositolgylcans, monoalkylglycerophosphoinositolglycans, 1Z-alkenylglycerophosphoinositolglycans, glycerophosphonocholines, diacylglycerophosphonocholines, 1-alkyl,2-acylglycerophosphonocholines, 1Z-alkenyl,2-acylglycerophosphonocholines, dialkylglycerophosphonocholines, monoacylglycerophosphonocholines, monoalkylglycerophosphonocholines, 1Z-alkenylglycerophosphonocholines, glycerophosphonoethanolamines, diacylglycerophosphonoethanolamines, 1-alkyl,2-acylglycerophosphonoethanolamines, 1Z-alkenyl, 2-acylglycerophosphonoethanolamines, dialkylglycerophosphonoethanolamines, monoacylglycerophosphonoethanolamines, monoalkylglycerophosphonoethanolamines, 1Z-alkenylglycerophosphonoethanolamines, di-glycerol tetraether phospholipids (caldarchaeols), glycerol-nonitol tetraether phospholipids, oxidized glycerophospholipids, oxidized glycerophosphocholines, and oxidized glycerophosphoethanolamines.

Sphingolipids may be characterized by a long-chain base (typically 12 to 26 carbon atoms) linked by an amide bond to a fatty acid and via a terminal hydroxyl group to complex carbohydrates or phosphorous functional groups. These lipids play important roles in signal transmission between cells and cell recognition. Example sphingolipids include sphing-4-enines (sphingosines), sphinganines, 4-hydroxysphinganines (phytosphingosines), sphingoid base homologs and variants, sphingoid base 1-phosphates, lysosphingomyelins and lysoglycosphingolipids, N-methylated sphingoid bases, sphingoid base analogs, ceramides, N-acylsphingosines (ceramides), N-acylsphinganines (dihydroceramides), N-acyl-4-hydroxysphinganines (phytoceramides), acylceramides, ceramide 1-phosphates, phosphosphingolipids, ceramide phosphocholines (sphingomyelins), ceramide phosphoethanolamines, ceramide phosphoinositols, phosphonosphingolipids, neutral glycosphingolipids, simple Glc series, GalNAcβ1-3Galα1-4Galβ1-4Glc- (globo series), GalNAcβ1-4Galβ1-4GLc- (ganglia series), Galβ1-3GlcNAcβ1-3Galβ1-4Glc- (lacto series), Galβ1-4GlcNAcβ1-3Galβ1-4Glc- (neolacto series), GalNAcβ1-3Galα1-3Galβ1-4Glc- (isoglobo series), GlcNAcβ1-2Manβ1-3Manβ1-4Glc- (mollu series), GalNAcβ1-4GlcNacβ1-3Manβ1-4Glc- (arthro series), acidic glycosphingolipids, gangliosides, sulfoglycosphingolipids (sulfatides), glucuronosphingolipids, phosphoglycosphingolipids, basic glycosphingolipids, amphoteric glycosphingolipids, and arsenosphingolipids.

Saccharolipids may be comprised of fatty acids linked directly to a sugar backbone. Typically, a monosaccharide takes the place of the glycerol molecule that forms the backbone of other lipids such as glycerolipids and glycerophospholipids. Saccharolipids play a role in the bilayer structure of cell membranes. Example saccharolipids include acylaminosugars, monoacylaminosugars, diacylaminosugars, triacylaminosugars, tetraacylaminosugars, pentaacylaminosugars, hexaacylaminosugars, heptaacylaminosugars, acylaminosugar glycans, acyltrehaloses, and acyltrehalose glycans.

Glycoglycerolipids may be comprised of fatty acids linked through an ester oxygen to the first and second carbons of a glycerol molecule, with a carbohydrate functional group ester-linked to the third carbon atom. The carbohydrate functional group may include one or more sugar monomers. Other functional groups may also be linked to the carbohydrate functional group. Example glycoglycerolipids include monogalactosyldiacylglycerols, digalactosyldiacylglycerols, trigalactosyldiacylglycerols, tetragalactosyldiacylglycerols, polygalactosyldiacylglycerols, monoglucosyldiacylglycerols, diglucosyldiacylglycerols, monogalactosylmonoacylglycerols, digalactosylmonoacylglycerols, sulfoquinovosyldiacylglycerols, acylsulfoquinovosyldiacylglycerols, acylgalactosylglucosyldiacylglycerols, kojibiosyldiacylglycerols, galactofuranosyldiacylglycerols, galactopyranosyldiacylglycerols, 1,2-diacyl-3-O-a-D-glucuronyl-sn-glycerols, glucosylglucuronyldiacylglycerols, galacturonyldiacylglycerols, polyglucosyldiacylglycerols, and monoglucosyldiacylglycerols.

Sterol esters may be characterized as comprising alcohols sharing a fused four-ring steroid structure ester-linked to one or more fatty acyls. Examples include cholesteryl esters, campesterol esters, stigmasterol esters, sitosterol esters, avenasterol esters, fucosterol esters, isofucosterol esters, and ethylcholesteryl esters.

FIG. 1 illustrates a general flow chart of various embodiments of a method 100 of the present invention. At step 105, lipids are introduced into a reaction chamber. A saponification reaction occurs when a base is added to the reactor at step 110. One or more alcohols may be present during the saponification reaction (step 110) to aid in the formation of a homogeneous mixture of the lipids and the base. The product of the saponification reaction is one or more alkali soaps (step 115).

In general, saponification is the hydrolysis of esters under basic conditions. Using a triacylglycerol as an example (shown in Equation 1), in the presence of a base such as sodium hydroxide the fatty acid groups are stripped from the glycerol backbone by hydrolysis to form fatty acid salts (alkali soaps) and glycerol as reaction products.

$$C_3H_5(COOR)_3+3NaOH\rightarrow 3\ RCOO^-+3\ Na^++C_3H_5(OH)_3 \quad \text{Equation 1}$$

If the saponification reaction described in the previous paragraph is performed in the presence of an alcohol and in the absence of water, and if a quantity of base sufficient to convert a portion of the alcohol to an alkoxide and to also act as a catalyst is present, any saponifiable lipids present may be transesterified directly to fatty esters. Using a triacylglycerol as an example (shown in Equation 2), in the presence of an alcohol and a base such as sodium hydroxide the fatty acid carbonyl groups are subject to nucleophilic attack and subsequent replacement of the glycerol with the alcohol.

$$C_3H_5(COOR)_3+3\ R'OH+OH^-\rightarrow 3\ RCOOR'+C_3H_5(OH)_3+OH^- \quad \text{Equation 2}$$

The alkali soaps are then reacted with one or more alcohols in the presence of an acid in an esterification reaction at step 120. In various embodiments, the acid is a mineral acid. The acid neutralizes any residual base, converts alkali soaps into free fatty acids, and catalyzes the reaction. The acid may also serve as a dehydrating agent to sequester any water byproduct of the esterification reaction. The product of the esterification reaction is typically one or more fatty esters (step 125).

Esterification is simply the chemical process of producing esters. Most commonly, esters are formed from a fatty acid and an alcohol. In the example above, after neutralization the carbonyl group of the alkali soap reacts with the alcohol according to Equation 3 to form one or more fatty esters (RCOOR').

$$RCOO^-+R'OH+2H+\rightarrow RCOOH+R'OH+H^+\rightarrow RCOOR'+H^++H_2O \quad \text{Equation 3}$$

Figure 2:
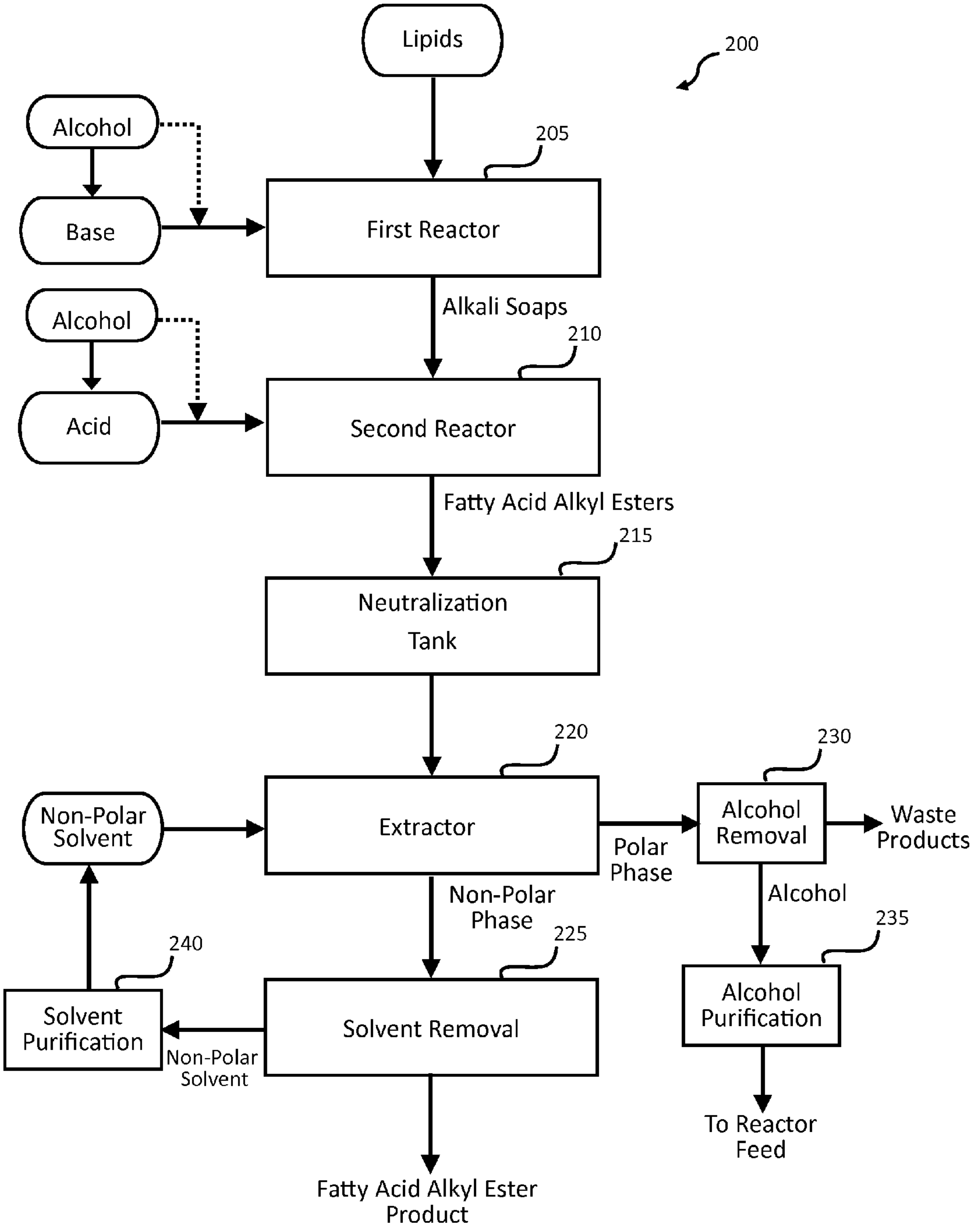
FIG. 2 is a flowchart of a method for converting lipids comprising fatty acids into fatty esters according to various embodiments of the present invention.

FIG. 2 illustrates an exemplary method 200 of producing fatty esters from saponifiable lipids according to various embodiments of the present invention. At step 205, saponifiable lipids are introduced into a reaction chamber. In various embodiments, the saponifiable lipids are the product of an extraction process involving various algae species. Algae are mostly aquatic photosynthetic organisms that range from microscopic flagellate to giant kelp. Algae may be loosely grouped into seven categories: Euglenophyta (euglenoids), Chrysophyta (golden-brown algae), Pyrrophyta (fire algae), Chlorophyta (green algae), Rhodophyta (red algae), Paeophyta (brown algae), and Xanthophyta (yellow-green algae). Lipid extracted from any algae species may be used in the various embodiments of the present invention, including *Amphora, Anabaena, Anikstrodesmis, Botryococcus, Chaetoceros, Chlorella, Chlorococcum, Cyclotella, Cylindrotheca, Dunaliella, Emiliana, Euglena, Glossomastix, Hematococcus, Isochrysis, Monochrysis, Monoraphidium, Nannochloris, Nannochloropsis, Navicula, Nephrochloris, Nephroselmis, Nitzschia, Nodularia, Nostoc, Oochromonas, Oocystis, Oscillartoria, Pavlova, Phaeodactylum, Picochloris, Platymonas, Pleurochrysis, Porhyra, Pseudoanabaena, Pyramimonas, Scenedesmus, Stichococcus, Synechococcus, Synechocystis, Tetraselmis, Thalassiosira*, and *Trichodesmium.*

Additionally, lipids from non-algae sources, such as plant oils and animal oils may also be used in various embodiments, as may various petroleum-based products and synthetic oils. Non-limiting examples of sources of non-algae lipids include fish oil, tung oil, colza oil, soy bean oil, corn oil, peanut oil, palm oil, rape seed oil, sunflower oil, safflower oil, corn oil, mineral oil, coconut oil, linseed oil, olive oil, sesame seed oil, animal fats, frying oil waste, sewage sludge, and the like.

One or more bases may be added to the reactor at step 205, which may initiate the saponification reaction discussed above. In various embodiments, one or more alcohols may be also be added at step 205. The base (or mixture of bases) may be any compound that is capable of supplying hydroxyl ions ($OH^-$) to the reaction. Strong bases (compounds which dissociate completely) may tend to accelerate the rate of the saponification reaction and push the reaction more towards complete conversion of the lipids to alkali soaps. Non-limiting examples of strong bases are the hydroxides of alkali metals and alkaline earth metals, such as sodium hydroxide, potassium hydroxide, barium hydroxide, cesium hydroxide, strontium hydroxide, calcium hydroxide, lithium hydroxide, and rubidium hydroxide.

In some situations, various alkoxides ($RO^-$) also form strong bases and may be used in various embodiments. If alkoxides are used, the amount of transesterification may increase relative to the amount of saponification, increasing the proportion of fatty esters produced in the base reaction.

The most common alkoxides are sodium methoxide and potassium methoxide. Other alkoxides, for example those formed with the alkali metals and alkaline earth metals, may also be used in various embodiments. Using an alkoxide as the base may have an added benefit of limiting the amount of water present in the reactor (see the discussion below of the effect of water). Alkoxides readily react with water, producing an alcohol and hydroxide ions. Therefore, commercially available alkoxides are generally water-free.

The base may be added to the reactor either before or after the lipids are introduced into the reactor. Alternatively, the base may be premixed with the lipids before the reactor. In various embodiments, the base may be premixed with the alcohol prior to adding the mixture to the reactor. By premixing the base and the alcohol, the mixture can be cooled prior to introduction into the reactor, thereby avoiding localized hot spots before the reactor contents thoroughly mix.

The alcohol may serve to aid the formation of a homogeneous mixture of the lipids and the base. The alcohol (or mixture of alcohols) may be selected for compatibility with the base. For example, if a methoxide is the base, then methanol may be selected as the alcohol because methoxide is the conjugate base of methanol. In various embodiments, a wide variety of other alcohols may be used, such as alcohols with the general formula $C_nH_{2n+1}OH$. Examples of such alcohols include methanol, ethanol, propanol, butanol, etc. Alcohols in which one or more of the hydrogen atoms have been substituted with functional groups may also be suitable. Other embodiments may use other alcohols (having the general formula ROH), such as glycerol, various glycols, and other polyols. The R-group may be any alkyl or substituted alkyl group; primary, secondary, or tertiary; have an open-chain or cyclic structure; have carbon double bonds; halogen atoms; or an aromatic ring.

In various embodiments, the amount of the base required for the saponification reaction may be based, at least in part, on the amount and composition of the lipids. First, a stoichiometric amount of the base may be added to hydrolyze essentially all of the ester-linked lipids, including glycerolipids and other esters, to alkali soaps. Where the lipids are supplied from algae, the lipids may generally be fatty acyls (fatty acids), and the amount of the base should be sufficient to convert all of the fatty acyls to alkali soaps.

Second, in certain embodiments additional base may be added to function as a catalyst, promoting the formation of esters from alkali soaps and an alcohol. As shown in FIG. 1, first the ester-linked lipids are saponified using a strong base to alkali soaps, then the alkali soaps are esterified using an acid catalyst to fatty acid alkyl esters. However, since strong bases also catalyze transesterification, if the saponification reaction is conducted in an alcohol solvent some ester-linked lipids may be transesterified directly to fatty esters. Any fatty esters formed during the saponification reaction may simply flow through the esterification reaction and become part of the final product.

In various embodiments, the catalytic excess of the base added to the saponification reaction may range from about 0.1 percent to about 20 percent by weight of the total reactor contents (lipids, stoichiometric amount of the base, and the alcohol). Other ranges may also be suitable, such as from about 0.25 percent to about 5 percent by weight of the total reactor contents.

Returning to FIG. 2, the alkali soap product of the saponification reaction may be transported to a second reactor at step 210 for the esterification reaction. One or more acids may then be added to the reactor at step 210, which initiates the esterification reaction discussed above. One or more alcohols may also be added at step 210. In various embodiments, the acid may be a mineral acid. The mineral acid (or mixture of mineral acids) may be any compound that is capable of supplying hydrogen ions ($H^+$) to the reaction. Strong acids (compounds which completely dissociate into hydrogen ions and anions) may tend to accelerate the rate of the esterification reaction and push the reaction more towards complete conversion of the alkali soaps to fatty esters. Non-limiting examples of strong acids are sulfuric acid, hydrochloric acid, nitric acid, perchloric acid, hydrobromic acid, boron trifluoride, and hydroiodic acid.

Similar to the base added at step 205, the acid may be added to the reactor either before or after the alkali soaps are introduced into the reactor. In various embodiments, the acid may be premixed with the alcohol prior to adding the mixture to the reactor. By premixing the acid and the alcohol, the mixture can be cooled prior to introduction into the reactor, thereby avoiding localized hot spots before the reactor contents thoroughly mix.

The amount of acid added to the reactor at step 210 may depend on at least three factors. First, the acid may neutralize any excess, unreacted base from the saponification reaction. Once the excess base is neutralized, a stoichiometric amount of the acid may be added to convert the alkali soaps to fatty acids. Finally, the acid may be added as a catalyst. The catalytic excess of the acid may function to speed up the esterification reaction.

One or more alcohols may also be added at step 210. The alcohols discussed above for the saponification reaction may also be suitable for the esterification reaction. In various embodiments, the alcohols used in the saponification reaction are the same as the alcohols used in the esterification reaction. In other embodiments, the alcohols used for the two reactions may be different.

Following the esterification reaction, the reaction mixture may be acidic in nature, and removing the acidity may be beneficial for further processing. For example, the selection of materials of construction for pipes, tanks, pumps, etc. may be simplified if acidic conditions are not a consideration. Therefore, the fatty acid alkyl esters and other contents of the second reactor may be moved to a neutralization tank at step 215 after the esterification reaction. In various embodiments, the neutralization step is optional. At the neutralization tank, a base may be added to bring the pH of the tank contents to a neutral level. In various embodiments, the pH may be raised to within a range from about 5 to about 9. For process convenience and to avoid undesired side reactions, the base selected for the neutralization step may be the same base used in the saponification reaction. However, a different base may be used in various embodiments.

Following neutralization (or following the esterification reaction if there is no neutralization step), the fatty esters may be separated from the reaction mixture to form a more concentrated fatty ester product. This separation may occur in a liquid extraction system at step 220. A solvent may be added to the reaction mixture, which in some embodiments is a non-polar solvent. Non-polar solvents have insignificant electromagnetic activity, and are commonly classified as having a dielectric constant less than 15. Examples of non-polar solvents include hexane, cyclohexane, heptane, d-limonene, naphtha, xylene, toluene, pentane, cyclopentane, benzene, 1,4-dioxane, chloroform, diethyl ether, dichloromethane, tetrahydrofuran, methyl acetate, mixed methyl esters such as biodiesel, and ethyl esters such as ethyl acetate.

The addition of the non-polar solvent may cause the reaction mixture to separate into a polar phase and a non-polar phase. The fatty acid alkyl esters, being generally non-polar compounds, tend to migrate to the non-polar phase along with the non-polar solvent. A variety of methods, such as centrifugation, cyclone separation, bypass filtering, decanting, settling, and the like may be used either individually or in combination to effect the separation of the phases. A multi-stage liquid extractor, such as a staged mixer-settler or a counter-current extraction column, may also be used. After the two phases are separated, the non-polar phase may undergo further processing through a solvent removal operation at step 225. After solvent removal, a more concentrated fatty ester product may be produced. In various embodiments, the solvent recovered at the solvent removal operation (step 225) may be recycled for reuse in the extraction process (step 220). The recovered solvent may undergo one or more further purification operations (step 240) prior to reuse.

The polar phase recovered from the extractor (step 220) may contain any remaining alcohols from the saponification and esterification reactions. Similar to the extraction solvent, the recovered alcohols may be reused in the process and may require removal from other waste products (step 230) and further purification (step 235) prior to reuse.

The first and second reactor may be any suitable reactor known in the art. Example reactors are batch reactors, fixed-bed plug flow reactors, continuously stirred tank reactors, and the like. The reactor may be a section of pipe. In various embodiments, the reactor may be agitated by mechanical devices or non-mechanical processes such as ultrasonics. Reactors with static mixing such as reactors containing contact structures such as baffles, trays, packing, and other impingement structures may also be used. Each of the first and second reactors may be comprised of multiple reactors operated either in series or parallel. In various embodiments employing batch processing, one or more of the steps illustrated in FIG. 2 may occur in a single vessel. For example, the first and second reactor and the neutralization tank may all be the same vessel.

The saponification reaction and the esterification reaction may occur at ambient temperature or at elevated temperature. Elevated temperatures may tend to decrease reaction times. In various embodiments, the saponification reaction and the esterification reaction temperature may be maintained in the range from about 30° C. to about 200° C., or in the range from about 30° C. to about 140° C. Likewise, the neutralization (step 215), extraction (step 220), and solvent removal (step 225) may be carried out at elevated temperatures.

The pressure of each of the steps of FIG. 2 in various embodiments may be carried out at about atmospheric pressure, although some embodiments may be carried out at higher or lower pressures.

An exemplary computing system may be used to implement various embodiments of the systems and methods disclosed herein. The computing system may include one or more processors and memory. Main memory stores, in part, instructions and data for execution by a processor to cause the computing system to control the operation of the various elements in the systems described herein to provide the functionality of certain embodiments. Main memory may include a number of memories including a main random access memory (RAM) for storage of instructions and data during program execution and a read only memory (ROM) in which fixed instructions are stored. Main memory may store executable code when in operation. The system further may include a mass storage device, portable storage medium drive(s), output devices, user input devices, a graphics display, and peripheral devices. The components may be connected via a single bus. Alternatively, the components may be connected via multiple buses. The components may be connected through one or more data transport means. Processor unit and main memory may be connected via a local microprocessor bus, and the mass storage device, peripheral device(s), portable storage device, and display system may be connected via one or more input/output (I/O) buses. Mass storage device, which may be implemented with a magnetic disk drive or an optical disk drive, may be a non-volatile storage device for storing data and instructions for use by the processor unit. Mass storage device may store the system software for implementing various embodiments of the disclosed systems and methods for purposes of loading that software into the main memory. Portable storage devices may operate in conjunction with a portable non-volatile storage medium, such as a floppy disk, compact disk or Digital video disc, to input and output data and code to and from the computing system. The system software for implementing various embodiments of the systems and methods disclosed herein may be stored on such a portable medium and input to the computing system via the portable storage device. Input devices may provide a portion of a user interface. Input devices may include an alpha-numeric keypad, such as a keyboard, for inputting alpha-numeric and other information, or a pointing device, such as a mouse, a trackball, stylus, or cursor direction keys. In general, the term input device is intended to include all possible types of devices and ways to input information into the computing system. Additionally, the system may include output devices. Suitable output devices include speakers, printers, network interfaces, and monitors. Display system may include a liquid crystal display (LCD) or other suitable display device.

Display system may receive textual and graphical information, and processes the information for output to the display device. In general, use of the term output device is intended to include all possible types of devices and ways to output information from the computing system to the user or to another machine or computing system. Peripherals may include any type of computer support device to add additional functionality to the computing system. Peripheral device(s) may include a modem or a router or other type of component to provide an interface to a communication network. The communication network may comprise many interconnected computing systems and communication links. The communication links may be wireline links, optical links, wireless links, or any other mechanisms for communication of information. The components contained in the computing system may be those typically found in computing systems that may be suitable for use with embodiments of the systems and methods disclosed herein and are intended to represent a broad category of such computing components that are well known in the art. Thus, the computing system may be a personal computer, hand held computing device, telephone, mobile computing device, workstation, server, minicomputer, mainframe computer, or any other computing device. The computer may also include different bus configurations, networked platforms, multi-processor platforms, etc.

Various operating systems may be used including Unix, Linux, Windows, Macintosh OS, Palm OS, MS-DOS, MINIX, VMS, OS/2, and other suitable operating systems. Due to the ever changing nature of computers and networks, the description of the computing system is intended only as a specific example for purposes of describing embodiments. Many other configurations of the computing system are possible having more or less components.

As used herein, the terms "having", "containing", "including", "comprising", and the like are open ended terms that indicate the presence of stated elements or features, but do not preclude additional elements or features. The articles "a", "an" and "the" are intended to include the plural as well as the singular, unless the context clearly indicates otherwise.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

While the present invention has been described in connection with a series of preferred embodiments, these descriptions are not intended to limit the scope of the invention to the particular forms set forth herein. It will be further understood that the methods of the invention are not necessarily limited to the discrete steps or the order of the steps described. To the contrary, the present descriptions are intended to cover such alternatives, modifications, and equivalents as may be included within the spirit and scope of the invention as defined by the appended claims and otherwise appreciated by one of ordinary skill in the art.

EXAMPLE 1

A 1.5 molar potassium hydroxide (KOH) solution was prepared by dissolving 85.3 grams of potassium hydroxide in 844 milliliters of methanol. The solution was prepared in a three-neck round bottom flask equipped with a chilled condenser.

A 4.5 molar solution of sulfuric acid in methanol was prepared by slowly dripping 125 milliliters of concentrated sulfuric acid into 422 ml of methanol. The solution was prepared in a three-neck round bottom flask equipped with a chilled condenser. The flask was chilled in an ice bath during mixing.

A sample of crude algae oil weighing 422 grams was added to a 12 liter round bottom flask equipped with a condenser. The oil was heated until liquefied, and the previously prepared 1.5 molar potassium hydroxide in methanol solution was added. The flask was allowed to heat under reflux (about 63° C. to about 65° C.) at about atmospheric pressure for about one hour. The flask was removed from the heat and allowed to cool for about one hour before proceeding to esterification.

After the reaction mixture was cooled to about 55° C., the previously prepared 4.5 molar sulfuric acid in methanol solution was added slowly. The flask was allowed to heat under reflux (about 63° C. to about 65° C.) at about atmospheric pressure for about one hour. The flask was removed from the heat and allowed to cool for about one hour before proceeding to extraction.

Once the reaction mixture had cooled to about 55° C., the reaction mixture was transferred to a 4.5 liter Buchner funnel and the reaction mixture was filtered through a nominal 1.7 micron glass fiber filter paper. The solids were then washed with about 6 liters of hexane to remove any entrained oil. The solids-free reactor effluent was then mixed with 8 liters of hexane and stirred. The phases were then allowed to separate. The washing step was repeated twice more. The hexane fractions were combined, and the hexane was then removed by vacuum distillation.

After completion of the vacuum distillation, 121 grams of product was recovered. Further analysis showed that the product contained 74.65 grams of fatty acid methyl ester.

EXAMPLES 2 AND 3

Saponification: 10.0 grams of crude algae oil and 20.0 milliliters of a 1.34 molar solution of potassium hydroxide in methanol were mixed in a Fisher-Porter tube, which was then sealed and placed in a 100° C. water bath. A second Fisher-Porter tube was charged with the same components plus 1.5 grams of hexane, which was then sealed and placed in the water bath. Both tubes were placed in the water bath at the same time and left for 7.5 minutes after reaching reaction temperature (about 2 minutes). Each tube was shaken several times while in the water bath. There were no discernable visual differences between the two runs. Similar amounts of solids were present in each tube. The presence of hexane in one of the tubes appeared inconsequential, as no visible sign of an emulsion was present in either tube.

The tubes were removed from the water bath and the contents were cooled, followed by analysis via titration. A soap concentration of 31.23 percent was found in the hexane-free run, while the run containing hexane was found to have a soap concentration of 29.00 percent. After adjusting for dilution from the added hexane, the soap concentration was calculated to be 30.45 percent. Considering the difficult of the titration due to the darkness of the reaction mixtures, the soap concentrations in the two runs were considered to be equal.

Each run was sampled, derivatized with N-methyl-N-(trimethylsilyl)trifluroacetamide (MSTFA) and analyzed via gas chromatography according to American Society for Testing and Materials (ASTM) Method D6584. The two gas chromatograph scans were virtually identical and showed that all lipids initially present in the crude algae oil had been completely converted into their corresponding free fatty acids (FFAs). No traces of mono-, di-, or triglycerides were detected. Additionally, no steryl esters were detected. Saponification was considered complete in both runs.

Esterification: To each saponification reaction mixture was added a solution of 1.81 grams of concentrated sulfuric acid dissolved in 2.0 grams of anhydrous methanol. These acid solutions were prepared by slowly dripping the concentrated sulfuric acid into chilled methanol. This amount of acid was sufficient to convert all soaps back to their FFAs and to provide a sufficient excess of acid to catalyze esterification of those FFAs into their methyl esters. The Fisher-Porter tubes were re-sealed and heated, side-by-side, to 100° C. for 30 minutes. The tubes were shaken several times during the heating step. There were, again, no discernable visual differences between the two runs. Insoluble potassium sulfate ($K_2SO_4$), the co-product of the neutralization of the potassium soaps formed during saponification with the added sulfuric acid, was present in each reaction mixture. Most of this potassium sulfate appeared to dissolve at 100° C. but precipitated out of solution when the reaction mixtures were cooled to 50° C.

The reaction mixtures were cooled to 50° C., and samples were removed for gas chromatograph analysis. Derivatization was again performed using MSTFA to determine if any residual FFA remained. The chromatograms of the two reaction mixtures were virtually identical. Essentially all of the FFAs appeared as their methyl esters with only traces of FFAs remaining (appearing in the chromatograms as their TMS esters). Esterification was at least 99 percent complete. These analyses showed that the presence of 15 weight percent residual hexane in the algae oil does not interfere with either saponification or esterification. The short reaction times, 7.5 minutes for saponification and 30 minutes for esterification, showed that the required conversions were quite fast at 100° C. It was also likely that hexane levels greater than 15 percent in the starting algae oil would be permissible.

What is claimed is:

1. A method of converting saponifiable lipids into fatty esters, comprising:

reacting the lipids with a base in presence of a first alcohol to form alkali soaps; and reacting the alkali soaps with an acid in the presence of a second alcohol to form fatty esters; and wherein at least a portion of the lipids is derived from algal oils.

2. The method of claim 1, wherein the saponifiable lipids are fatty acids which are either free fatty acids or are ester-linked to a sterol or a glycerol backbone.

3. The method of claim 1, wherein at least a portion of the algal oil is produced from the algal species *Amphora, Anabaena, Anikstrodesmis, Botryococcus, Chaetoceros, Chlorella, Chlorococcum, Cyclotella, Cylindrotheca, Dunaliella, Emiliana, Euglena, Glossomastix, Hematococcus, Isochrysis, Monochrysis, Monoraphidium, Nannochloris, Nannochloropsis, Navicula, Nephrochloris, Nephroselmis, Nitzschia, Nodularia, Nostoc, Oochromonas, Oocystis, Oscillartoria, Pavlova, Phaeodactylum, Picochloris, Platymonas, Pleurochrysis, Porhyra, Pseudoanabaena, Pyramimonas, Scenedesmus, Stichococcus, Synechococcus, Synechocystis, Tetraselmis, Thalassiosira*, or *Trichodesmium.*

4. The method of claim 1, further comprising maintaining a reaction temperature between about 30° C. and about 140° C.

5. The method of claim 1, wherein at least one of the first alcohol and the second alcohol is comprised of more than one alcohol.

6. The method of claim 1, wherein both the first alcohol and the second alcohol are methanol.

7. The method of claim 1, further comprising mixing the base with the first alcohol prior to the lipids' reaction and mixing the acid with the second alcohol prior to the alkali soaps' reaction.

8. The method of claim 1, wherein an amount of the first alcohol is between about 0.25 times and about 10 times a weight of the lipids.

9. The method of claim 1, further comprising:

adding a non-polar solvent to produce a polar phase and a non-polar phase, whereby the fatty esters are contained predominantly in the non-polar phase;

separating the polar phase and the non-polar phase; and separating the fatty acid alkyl esters and the non-polar solvent from the non-polar phase.

10. The method of claim 9, wherein the non-polar solvent is hexane.

11. The method of claim 1, wherein the base is a methoxide.

12. The method of claim 1, wherein the acid is a mineral acid.

13. The method of claim 1, wherein the acid is selected from the group consisting of sulfuric acid, hydrochloric acid, nitric acid, boric acid, hydrofluoric acid, hydrobromic acid, perchloric acid, hydroiodic acid and mixtures thereof.

14. A method for converting saponifiable lipids into fatty esters, comprising:

adding a predetermined amount of saponifiable lipids to a reaction vessel;

in presence of a first alcohol, adding an amount of base sufficient to convert the lipids to alkali soaps;

adding a catalytic excess of the base equal to about 0.25 percent to about 5 percent of a total weight of the lipids, the stoichiometric amount of the base, and the first alcohol;

in presence of a second alcohol, adding a stoichiometric amount of an acid to neutralize excess base and to convert the alkali soaps to fatty acids; and adding a catalytic excess of the acid equal to about 0.5 percent to about 5 percent of a total weight of the lipids, the stoichiometric amount of the base, the catalytic excess of the base, and the first and second alcohols; and wherein at least a portion of the lipids is derived from algal oils.

15. The method of claim 14, wherein a total amount of the first alcohol and the second alcohol is between about 0.25 times and about 10 times the weight of the lipids.

16. The method of claim 14, wherein the first alcohol and the second alcohol are the same.

17. The method of claim 14, wherein the base is sodium methoxide or potassium methoxide, and the acid is sulfuric acid or hydrochloric acid.

18. The method of claim 14, further comprising maintaining an amount of water in the reaction vessel to less than 3 percent by weight of the lipids.

19. A method for converting saponifiable lipids into fatty esters, comprising:

determining a composition of the lipids;

adding a predetermined weight of lipids to a reaction vessel;

adding a base and a predetermined amount of an alcohol to the reaction vessel to form alkali soaps, the predetermined amount of the alcohol based on the composition of the lipids; and adding an acid to the reaction vessel to convert the alkali soaps to fatty esters; and wherein at least a portion of the lipids is derived from algal oils.

* * * * *